United States Patent
Barnes et al.

(10) Patent No.: US 12,103,851 B2
(45) Date of Patent: Oct. 1, 2024

(54) INK COMPOSITIONS BASED ON GRAPHENE AND A STABILISING AGENT AND SENSORS FABRICATED FROM THE INK

(71) Applicant: ALTERED CARBON LIMITED, London (GB)

(72) Inventors: Frazer John Barnes, London (GB); Ali Rohafza, London (GB)

(73) Assignee: Altered Carbon Limited, London (GB)

( * ) Notice: Subject to any disclaimer, the term of this patent is extended or adjusted under 35 U.S.C. 154(b) by 575 days.

(21) Appl. No.: 17/430,772

(22) PCT Filed: Feb. 13, 2020

(86) PCT No.: PCT/GB2020/050333
§ 371 (c)(1),
(2) Date: Aug. 13, 2021

(87) PCT Pub. No.: WO2020/165588
PCT Pub. Date: Aug. 20, 2020

(65) Prior Publication Data
US 2022/0162074 A1    May 26, 2022

(30) Foreign Application Priority Data
Feb. 13, 2019   (GB) ..................................... 1901958

(51) Int. Cl.
| C09D 11/106 | (2014.01) |
| C01B 32/194 | (2017.01) |
| C09D 11/38 | (2014.01) |
| C09D 11/52 | (2014.01) |
| C09D 139/06 | (2006.01) |
| G01N 27/12 | (2006.01) |

(52) U.S. Cl.
CPC .......... *C01B 32/194* (2017.08); *C09D 11/106* (2013.01); *C09D 11/38* (2013.01); *C09D 11/52* (2013.01); *C09D 139/06* (2013.01); *C01B 2204/22* (2013.01); *C01B 2204/32* (2013.01); *G01N 27/125* (2013.01)

(58) Field of Classification Search
CPC . C01B 32/194; C01B 32/192; C01B 2204/22; C01B 2204/32; C09D 11/106; C09D 11/38; C09D 11/52; C09D 139/06; C09D 11/324; C09D 7/61; C09D 11/02; G01N 27/125; G01N 33/0036; G01N 27/12; G01N 27/407; G01N 27/4075; B82Y 15/00; B82Y 40/00

USPC ......................................................... 524/495
See application file for complete search history.

(56) References Cited

U.S. PATENT DOCUMENTS

| 2013/0133934 A1* | 5/2013 | Flores ................... C09D 11/38 252/514 |
| 2015/0141666 A1* | 5/2015 | Chen ...................... H01M 4/96 549/12 |
| 2017/0037257 A1* | 2/2017 | Yang .................... C09D 5/1618 |
| 2017/0217775 A1* | 8/2017 | Sohn ..................... C01B 32/192 |
| 2017/0298523 A1* | 10/2017 | Hoffmann ............. C25B 11/043 |
| 2018/0327618 A1* | 11/2018 | McManus .............. C09D 11/30 |

FOREIGN PATENT DOCUMENTS

| CN | 104479456 A | 4/2015 |
| CN | 106680328 A | 5/2017 |
| CN | 106752380 A | 5/2017 |
| CN | 106928773 A | 7/2017 |
| CN | 107340362 A | 11/2017 |
| CN | 108641486 A | 10/2018 |
| CN | 108753043 A | 11/2018 |
| CN | 108760851 A | 11/2018 |
| CN | 108802111 A | 11/2018 |
| KR | 20190005028 A | 1/2019 |
| WO | 2016098942 A1 | 6/2016 |
| WO | 2017/025697 A1 | 2/2017 |

OTHER PUBLICATIONS

Rodgers, Peter et al: "The rise of graphene. A Collection of Reviews from Nature Journals, In: 1 Nanoscience and Technology . A Collection of Reviews from Nature Journals". Aug. 1, 2009 (Aug. 1, 2009). Co-Published with Macmillan Publishers Ltd. UK. XP055682650. ISBN: 978-981-4287-00-5, pp. 11-19. DOI: 10.1142/9789814287005_0002. Section: 11 Abstract11; p. 1.

Santra, S et al: "CMOS integration of inkjet-printed graphene for humidity sensing", Scientific Reports,vol. 5. No. 1, Nov. 30, 2015 (Nov. 30, 2015), XP055682270, DOI: 10.1038/srepl7374 figures 1, 6 Section: "Results"; p. 2-p. 8.

(Continued)

*Primary Examiner* — Hannah J Pak
(74) *Attorney, Agent, or Firm* — Dinsmore & Shohl LLP (57) ABSTRACT

Graphene based sensor technology is described. Certain aspects relate to graphene containing ink formulations suitable for fabricating sensor electrodes via inkjet printing methods and to sensor electrodes produced from such ink formulations. Certain further aspects relate to processes for fabricating functionalized graphene materials for use in such ink formulations. Further still, certain aspects relate to sensors comprising graphene sensor electrodes.

17 Claims, 7 Drawing Sheets

(56) References Cited

OTHER PUBLICATIONS

Bhangare Bhagyashri et al: "Evaluation of Humidity Sensor Based on PVP-RGO Nanocomposites". IEEE Sensors Journal, IEEE Service Center, New York, NY, US, vol. 18, No. 22, Nov. 15, 2018 (Nov. 15, 2018), pp. 9097-9104, XP011701867, ISSN: 1530-437X, DOI: 10.1109/JSEN.2018.2870324, [retrieved on Oct. 22, 2018] figures 1, 3, 4, Section: "II: Experimental"; p. 9097-p. 9098.

Juntunen, Taneli et al: Inkjet Printed Large-Area Flexible Few-Layer Graphene Thermoelectrics 11, Advanced Functional Materials, vol. 28, No. 22, Apr. 19, 2018 (Apr. 19, 2018), p. 1800480, XP055684334, DE ISSN: 1616-301X, DOI: 10.1002/adfm. 201800480, figures lb, 3b, p. 6.

Choi et al; Graphene-based gas sensors, ACS Appl. Nano Mater. 2020, 3, 2257?2265.

Varghese et al, Recent advances in graphene based gas sensors, Sensors and Actuators B:Chemical (2015), http://dx.doi.org/10.1016/j.snb.2015.04.062.

Li et al, (2017) "Improving the sensitive property of graphene-based gas sensor by illumination and heating", Sensor Review, vol. 37 Issue: 2, pp. 142-146.

Donarelli et al.,2D Materials for Gas Sensing Applications, Sensors, Oct. 18, 2018, 45 pages.

Kumar, Nanjundan Ashok, Synthesis of high quality reduced graphene oxide nanosheets free of paramagnetic metallic impurities; www.rsc.org/MaterialsA; 7 pages.

\* cited by examiner

Sensor 1 - NH₃ Measurements

Sensor 1 – NO₂ and SO₂ Measurements

Fig. 5

Sensor 2 - NH₃ Measurements

Sensor 2 – NO₂ and SO₂ Measurements

Fig. 6

Sensor 3 - NH₃ Measurements

Sensor 3 – NO₂ and SO₂ Measurements

Fig. 7

Sensor 4 - NH₃ Measurements

Sensor 4 – NO₂ and SO₂ Measurements

Fig. 8

| NO$_2$ concentration (ppb) | Resistance change (KΩ) | | | |
|---|---|---|---|---|
| | Sensor 1 | Sensor 2 | Sensor 3 | Sensor 4 |
| 45 | 48.11±2.2 | 42.39±1.5 | 90.33±2.4 | 427.36±9.7 |
| 100 | 43.82±1.4 | 38.21±2.0 | 81.71±1.8 | 335.06±1.6 |

| SO$_2$ concentration (ppb) | Resistance change (KΩ) | | | |
|---|---|---|---|---|
| | Sensor 1 | Sensor 2 | Sensor 3 | Sensor 4 |
| 45 | 28.54±1.0 | 26.09±1.3 | 72.74±1.9 | 223.38±6.5 |
| 100 | 35.93±1.6 | 14.37±0.7 | 78.32±1.3 | 196.9±6.0 |

INK COMPOSITIONS BASED ON GRAPHENE AND A STABILISING AGENT AND SENSORS FABRICATED FROM THE INK

CROSS-REFERENCE TO RELATED APPLICATIONS

This application is the U.S. National Stage of PCT/GB2020/050333 filed Feb. 13, 2020, which claims priority to United Kingdom Application No. 1901958.7, filed Feb. 13, 2019, the content of both are incorporated herein by reference in their entirety.

FIELD OF THE INVENTION

The present specification relates to graphene based sensors. Certain aspects relate to graphene containing ink formulations suitable for fabricating sensor electrodes via inkjet printing methods and to sensor electrodes produced from such ink formulations. Certain further aspects relate to processes for fabricating functionalized graphene materials for use in such ink formulations. Further still, certain aspects relate to sensors comprising graphene sensor electrodes.

BACKGROUND OF THE INVENTION

Due to their physical, chemical, and electrical properties, graphene materials have been already been proposed for next generation sensors. For example, graphene based electrochemical sensors, such as gas sensors, have been discussed in a number of publications including: "Graphene-based gas sensors", Journal of Materials Chemistry A, issue 35, 2013; "Recent advances in graphene based gas sensors", Sensors and Actuators B: Chemical, Volume 218, 31 Oct. 2015; "Improving the sensitive property of graphene-based gas sensor by illumination and heating", Sensor Review, Vol. 37, Issue 2, 2017; "2D Materials for Gas Sensing Applications", Sensors, 18, 2018. There are also many publications discussing the use of graphene based sensors for electrochemical sensing in a liquid environment.

The present specification describes formulations and fabrication techniques which enable low cost, low temperature, green chemistry fabrication routes to graphene based sensors which exhibit high levels of sensitivity and selectivity for a variety of target species and without requiring high temperature operation.

SUMMARY OF THE INVENTION

According to an aspect of the invention as described herein there is provided an ink for fabricating a sensor electrode, the ink comprising: water; polyvinylpyrrolidone (PVP); and a graphene material. PVP has been found to be surprisingly advantageous for graphene-based sensors as it combines several key functional requirements: (i) PVP functions as a stabilising agent to prevent graphene flakes from agglomerating in an ink formulation for printing of a sensor electrode enabling low cost, low temperature, green chemistry, inkjet printing fabrication routes to graphene based sensors; (ii) PVP has been found to improve electrode performance when compared to other stabilized graphene compositions in terms of providing a suitable electrode sensing surface for concentrating species to be sensed, i.e. PVP functions as a concentrating agent at the surface of a graphene based sensing electrode; and (iii) sensing electrodes comprising graphene and PVP have been found to have high levels of sensitivity and selectivity for a variety of target species without requiring high temperature operation.

According to a further aspect described herein there is provided a sensor electrode formed by printing of the ink formulation onto a suitable substrate and curing. The sensor electrode comprises PVP and a graphene material. As previously stated, an advantage of using PVP as a stabilizing agent for the graphene material in the ink formulation is that the presence of PVP in the resultant sensor electrode has been found to improve sensor electrode performance. The PVP seems to act as a concentrating agent at the surface of the graphene-based sensing electrode and sensing electrodes comprising a graphene material and PVP have been found to have high levels of sensitivity and selectivity for a variety of target species without requiring high temperature operation.

The graphene material can be provided in the form of a reduced graphene oxide material. For certain sensing applications it has been found that sulphur-doped graphene material is advantageous. Further still, it has been found that thiourea and/or sulfamic acid dopant significantly improves sensor electrode performance when compared to other sulphur dopants. Such a treated graphene material can also be combined with a metal (or metal salt) functionalization to grow metal containing nano-structures on the graphene surface. Such a treated and functionalized graphene material has been found to be advantageous for sensing applications. As such, another aspect of the invention as described herein provides a functionalized graphene material and a process for fabricating the functionalized graphene material, the process comprising: treating a graphene material with sulfamic acid and/or thiourea; and growing metal containing nanostructures on the surface of the treated graphene material.

Yet a further aspect of the present invention as described herein is a sensor comprising one or more sensor electrodes. Multiple electrodes having different compositions can be provided to provide optimized detection of multiple target species. Furthermore, electrode compositions can be tailored for different concentration ranges of particular target species in end applications.

In addition to the above, it has also been found that graphene sensor electrodes such as those described herein can be driven in such a manner as to readily clean the electrode. As such, in accordance with another aspect of the invention as described herein, there is provided a sensor comprising: a sensor electrode comprising graphene material, and a controller for providing a drive signal to the sensor electrode in order to sense species adhered to the sensor electrode, wherein the controller is further configured to apply a cleaning voltage to the sensor electrode, the cleaning voltage having a frequency in a range 100 Hz to 100 kHz and a magnitude in a range 1 to 60 V, optionally 1 to 20 V, to induce heating of the sensor electrode which removes one or more species adhered to the sensor electrode.

BRIEF DESCRIPTION OF THE DRAWINGS

To assist understanding of the present disclosure and to show how embodiments may be put into effect, reference is made by way of example to the accompanying drawings in which.

DETAILED DESCRIPTION OF THE INVENTION

As described in the summary section, according to one aspect of the invention there is provided an ink for fabricating a sensor electrode, the ink comprising: water; polyvinylpyrrolidone (PVP); and a graphene material. PVP has been found to be surprisingly advantageous for graphene-based sensors as it combines several key functional requirements: (i) PVP functions as a stabilising agent to prevent graphene flakes from agglomerating in an ink formulation for printing of a sensor electrode enabling low cost, low temperature, green chemistry, inkjet printing fabrication routes to graphene based sensors; (ii) PVP has been found to improve electrode performance when compared to other stabilized graphene compositions in terms of providing a suitable electrode sensing surface for concentrating species to be sensed, i.e. PVP functions as a concentrating agent at the surface of a graphene based sensing electrode; and (iii) sensing electrodes comprising graphene and PVP have been found to have high levels of sensitivity and selectivity for a variety of target species without requiring high temperature operation.

The specific type of PVP and the quantity of PVP within the ink formulations can be varied according to specification target species and sensor applications. For example, for certain sensors applications the PVP may have a chain length between 10 and 400, optionally between 10 and 100, and further optionally between 10 and 60. Furthermore, for certain applications the PVP may be provided in the ink formulation within a concentration range of 0.01 to 10 mg per ml of the ink, optionally within a concentration range of 0.1 to 1 mg per ml of the ink. Alternatively, the concentration of PVP may be expressed relative to the graphene concentration in the ink. For example, the PVP may be provided within a concentration range of 0.01 to 1 mg per mg of graphene, optionally within a concentration range of 0.04 to 0.4 mg per mg of graphene.

The graphene is advantageously provided in the form of flakes having a diameter in a range 1 to 20 micrometres, optionally 1 to 10 micrometres or 2 to 5 micrometres. The graphene can be processed by filtering to achieve graphene flakes having the desired size. Smaller flake sizes are removed as they are generally of lower quality. Larger flake sizes are removed so as to improve the flow characteristics of the resultant ink. The graphene material is typically provided within a concentration range of 0.5 to 50 mg per ml of the water, optionally 1 to 10 mg per ml of the water.

Typically the graphene material is several carbon layers thick rather than a perfect monolayer. Defects formed by the edges of atomic sheets in a multi-layer structure have been found to be useful in sensing applications as they provide binding sites on the surface of the graphene. That is, the graphene is in the form of flakes, each flake having a variable number of atomic carbon layers, rather than a perfect monolayer, thus providing binding sites at edges of atomic layers.

The graphene material can provided in the form of a reduced graphene oxide material. For certain sensing applications it has been found that sulphur-doped graphene material is advantageous. Further still, it has been found that thiourea and/or sulfamic acid dopant significantly improves sensor electrode performance when compared to other sulphur dopants. The sulphur dopant can be provided within a concentration range of 0.01 mg to 1 mg of sulphur dopant per 1 mg of graphene, optionally 0.15 mg-0.5 mg of sulphur dopant per 1 mg of graphene. The sulphur content of the starting graphene is generally selected to be very low such that a controlled amount of sulphur is added during the treatment with sulfamic acid and/or thiourea.

Advantageously, the graphene is treated to grow metal containing nano-structures (e.g. metal salt structures such as metal oxide structures) on the surface of the graphene. Examples of metals utilised in this process included one or more of yttrium, iron, strontium, molybdenum, cobalt, nickel, palladium, tin and tungsten. Surface structures vary according to the type of metal functionalisation and/or the type of sulphur-doping. Examples of metal containing surface structures include nano-clusters, flowers or clam-shell type nano-structures, and nanowire structures.

The preceding text describes aspects of the ink formulation. According to a further aspect described herein there is provided a sensor electrode formed by printing of the ink formulation onto a suitable substrate and curing. The sensor electrode comprises PVP and a graphene material. Details of the PVP and graphene materials are as described previously in relation to the ink used to form the sensor electrode. As previously stated, an advantage of using PVP as a stabilizing agent for the graphene material in the ink formulation is that the presence of PVP in the resultant sensor electrode has been found to improve sensor electrode performance. The PVP seems to act as a concentrating agent at the surface of the graphene-based sensing electrode and sensing electrodes comprising graphene and PVP have been found to have high levels of sensitivity and selectivity for a variety of target species without requiring high temperature operation.

The preceding text describes advantages of using PVP for graphene-based sensors. It was also described that thiourea and/or sulfamic acid dopant significantly improves sensor electrode performance when compared to other sulphur dopants and that this can be combined with a metal (or metal salt) functionalization to grow metal containing nano-structures on the graphene surface. Such a treated and functionalized graphene material has been found to be advantageous for sensing applications. Furthermore, while it has been found to be advantageous to use such a treated and functionalized graphene material in combination with PVP, it is also envisaged that such a treated and functionalized graphene material could be used with an alternative stabilization agent. As such, another aspect as described herein provides a functionalized graphene material and a process for fabricating the functionalized graphene material, the process comprising: treating a graphene material with sulfamic acid and/or thiourea; and growing metal containing nanostructures on the surface of the treated graphene material. Details of the form of graphene material and metal functionalization are as described in the preceding text in relation to the ink formulation. In accordance with this aspect, the use of PVP as a stabilization agent is advantageous but is not necessarily essential for certain applications of the treated and functionalized graphene material.

A further aspect as described herein is a sensor comprising one or more sensor electrodes. The sensor electrodes can be fabricated as previously described. Multiple electrodes having different compositions can be provided in a single sensor to provide optimized detection of multiple target species. Furthermore, electrode compositions can be tailored for different concentration ranges of particular target species in end applications. For example, different electrodes can be provided with different metal functionalization for different target species and/or a different sensing (concentration) range for a target species. As such, different sensors can be provided for different target species or a single sensor can be provided which has multiple electrodes for sensing different target species and/or different sensing ranges. Target species for end applications include one or more of $NH_3$, $NO_2$, $C_2H_4$, $CO_2$, $H_2S$, $SO_2$, CO, and VOCs (volatile organic compounds). Examples of metals utilised to functionalize the graphene for the target species included one or more of yttrium, iron, strontium, molybdenum, cobalt, nickel, palladium, tin and tungsten.

For example, for a $C_2H_4$ gas sensor it has been found to be useful to provide a metal functionalization using yttrium with iron and/or cobalt (the iron/cobalt added in the form of a chloride for example). By altering the amounts of yttrium and/or iron (III) chloride/cobalt chloride, the $C_2H_4$ gas concentration detection range can be modified.

For $CO_2$ and volatile organic compounds (VOCs), a strontium functionalization has been found to be useful. Strontium can be in the form of strontium nitrate. Cobalt chloride can also be added. Furthermore, optionally iron can also be added (e.g. in the form of iron (iii) chloride). The amount of strontium dictates the viscosity of the ink. Iron (iii) chloride has been found to increase detection of some VOCs and also $CO_2$, so therefore useful for indoor air quality monitoring.

For $NH_3$, a thiourea treated graphene material can be utilized. The amount of urea varies the $NH_3$ detection range. The electrode may also be treated with palladium (in the form of palladium chloride). However, too much thiourea and/or palladium shifts the electrode selectively between $NH_3$ and $NO_2$.

For $NO_2$, molybdenum or tungsten can be utilized for the metal functionalization. These metals can be provided in the form of sodium molybdenate and sodium tungstate. Molybdenum functionalization forms nanoflower type structures on the graphene. In contrast, tungsten functionalization forms nanowire type structures.

For $NO_2$ and $C_2H_4$, a cobalt-nickel functionalization can be utilized. Varying the amount of cobalt/nickel can finely tune the resultant electrode for either $NO_2$ or $C_2H_4$ selectivity.

Figure 1:
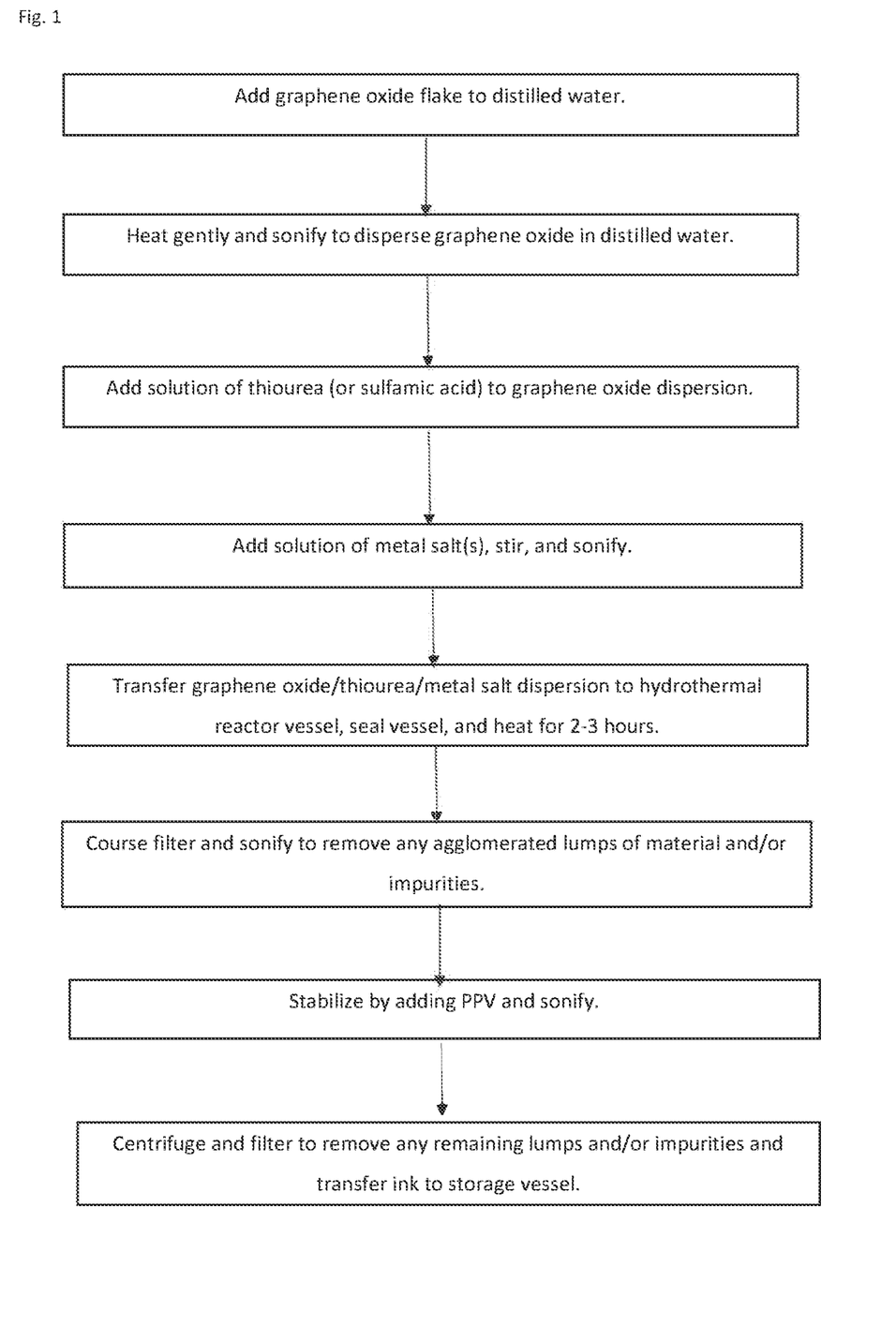
FIG. 1 shows a flow diagram illustrating a process for producing an ink formulation.

A typical process for producing an ink formulation is shown in FIG. 1. The process comprises the following steps:

Add graphene oxide flake to distilled water.

Heat gently and sonify to disperse graphene oxide in distilled water.

Add solution of thiourea (or sulfamic acid) to graphene oxide dispersion.

Add solution of metal salt(s), stir, and sonify.

Transfer graphene oxide/thiourea/metal salt dispersion to hydrothermal reactor vessel, seal vessel, and heat for 2-3 hours.

Course filter and sonify to remove any agglomerated lumps of material and/or impurities.

Stabilize by adding PPV and sonify.

Finally, centrifuge and filter to remove any remaining lumps and/or impurities and transfer ink to storage vessel.

Qualities for the thiourea/sulfamic acid, PPV, and the type and quantity of metal salts are within the ranges previously described and can be fine-tuned for particular applications, target species types, and target species concentration ranges.

Figure 2:
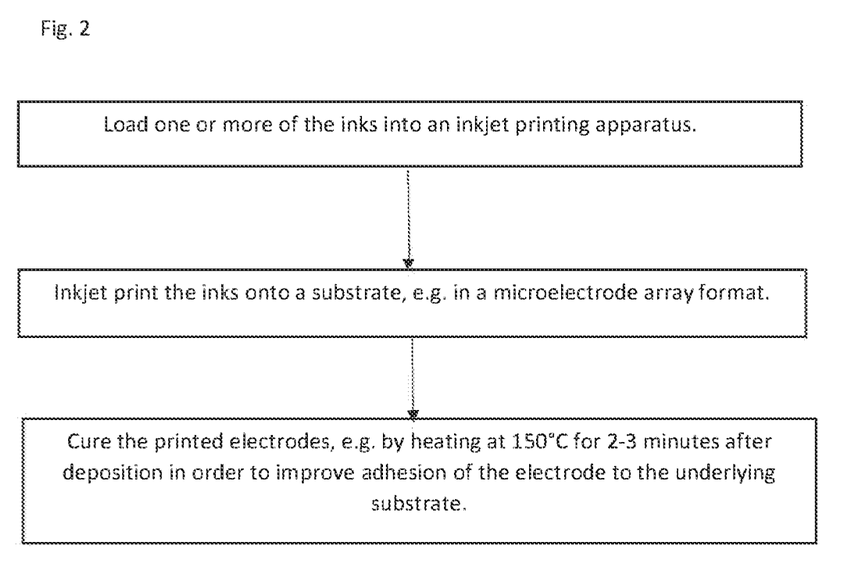
FIG. 2 shows a flow diagram illustrating a process for producing a sensor electrode using an ink formulation.

The resultant inks can be inkjet printed onto a suitable substrate to form electrodes. Typical substrates include: silicon; ceramic; fibreglass; Teflon; polyethylene terephthalate; and mica. The inkjet system approach provides a droplet based printing process that can be used on many different substrates. A typical process for producing a sensor electrode is shown in FIG. 2. The process comprises the following steps:

Load one or more of the inks into an inkjet printing apparatus.

Inkjet print the inks onto a substrate, e.g. in a microelectrode array format.

Cure the printed electrodes, e.g. by heating at 150° C. for 2-3 minutes after deposition in order to improve adhesion of the electrode to the underlying substrate.

Different compositions can be utilised to deposit a series of electrodes having different chemical compositions, metallic surface structures, and sensitivity to different target species. A graphene reference electrode can also be deposited in order to function as a sensor reference. The fabrication process is low temperature and low cost and the resultant sensors can also operate at relatively low temperatures compared to prior art graphene sensors which are heated to higher temperatures in operation.

A range of potential electrode structures are envisaged including microelectrode electrode arrays, interdigitated electrodes, and macro-electrodes. Micro-electrodes are usually preferred for most applications.

Figure 3:
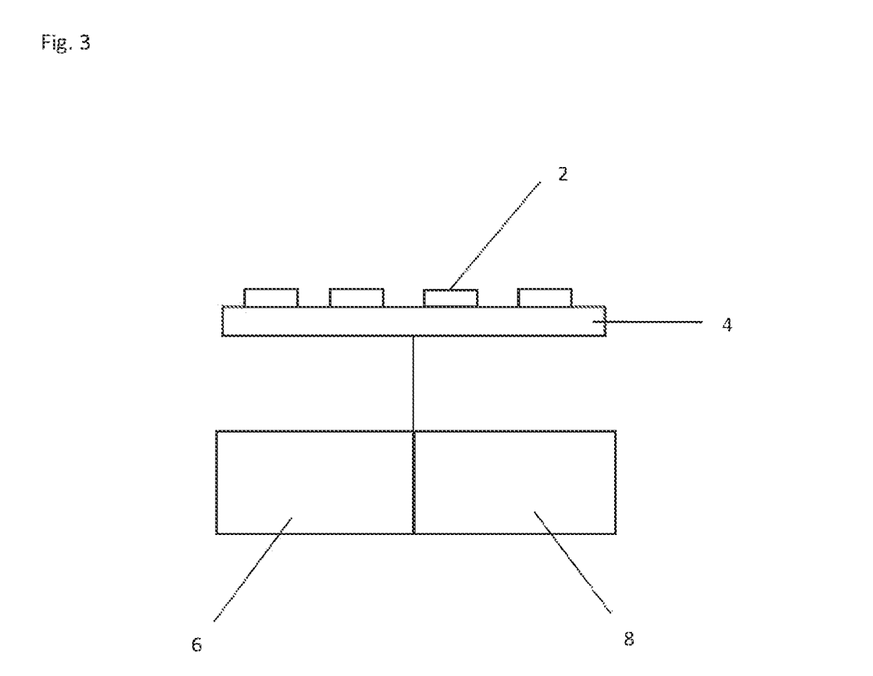
FIG. 3 shows a schematic of a sensor; and d.
Figure 4:
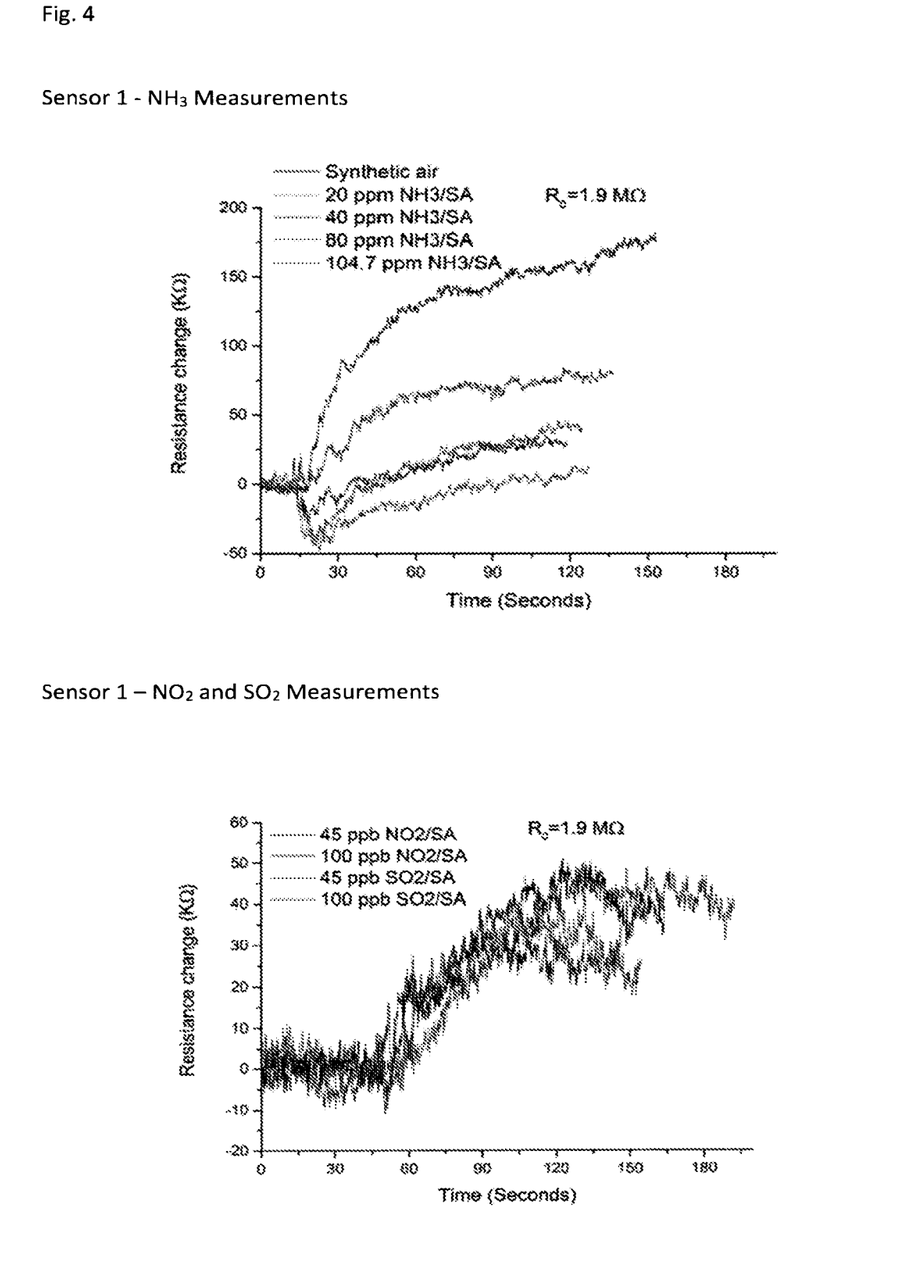
FIGS. 4 to 8 show resistance measurement results for four sensors fabricated as described herein—$NH_3$, $NO_2$, and $SO_2$ measurements were performed for each sensor.
Figure 5:
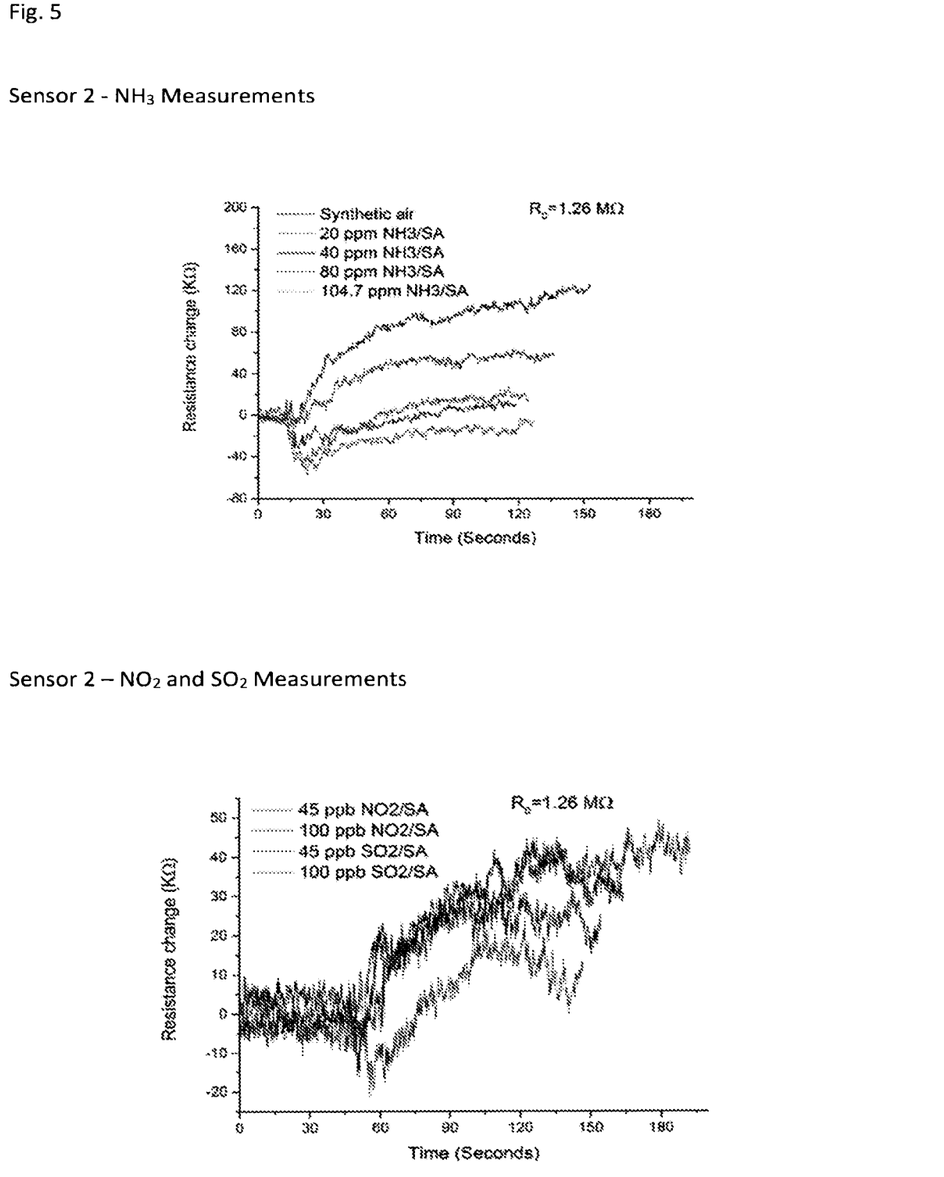
Figure 6:
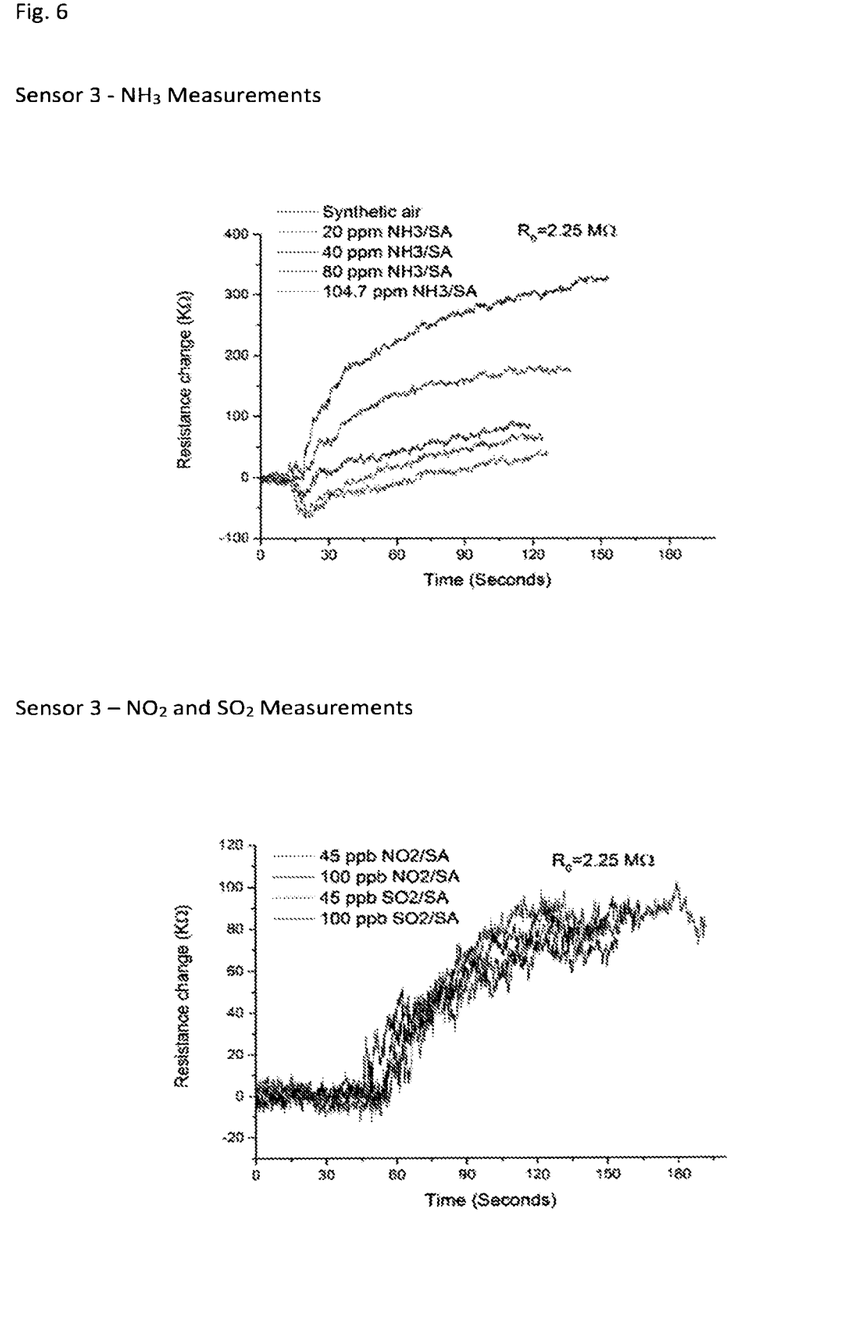
Figure 7:
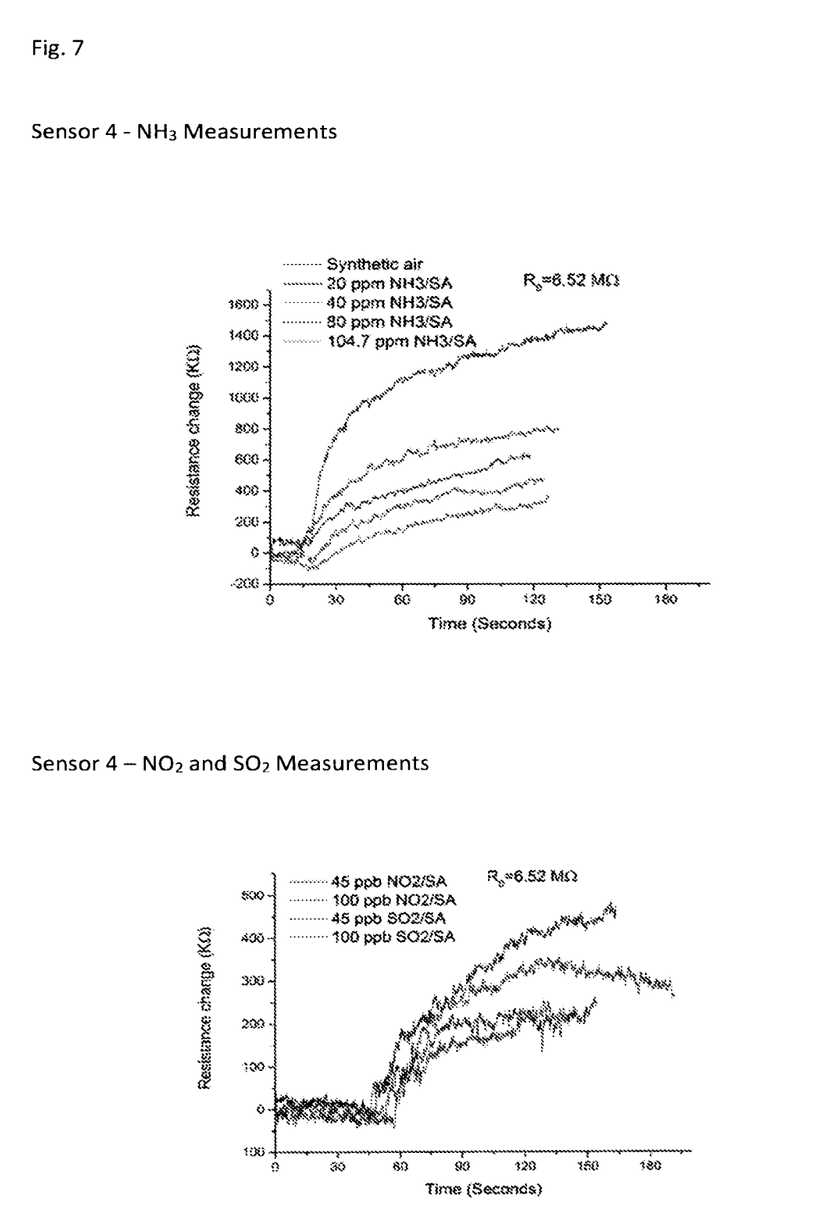
Figure 8:
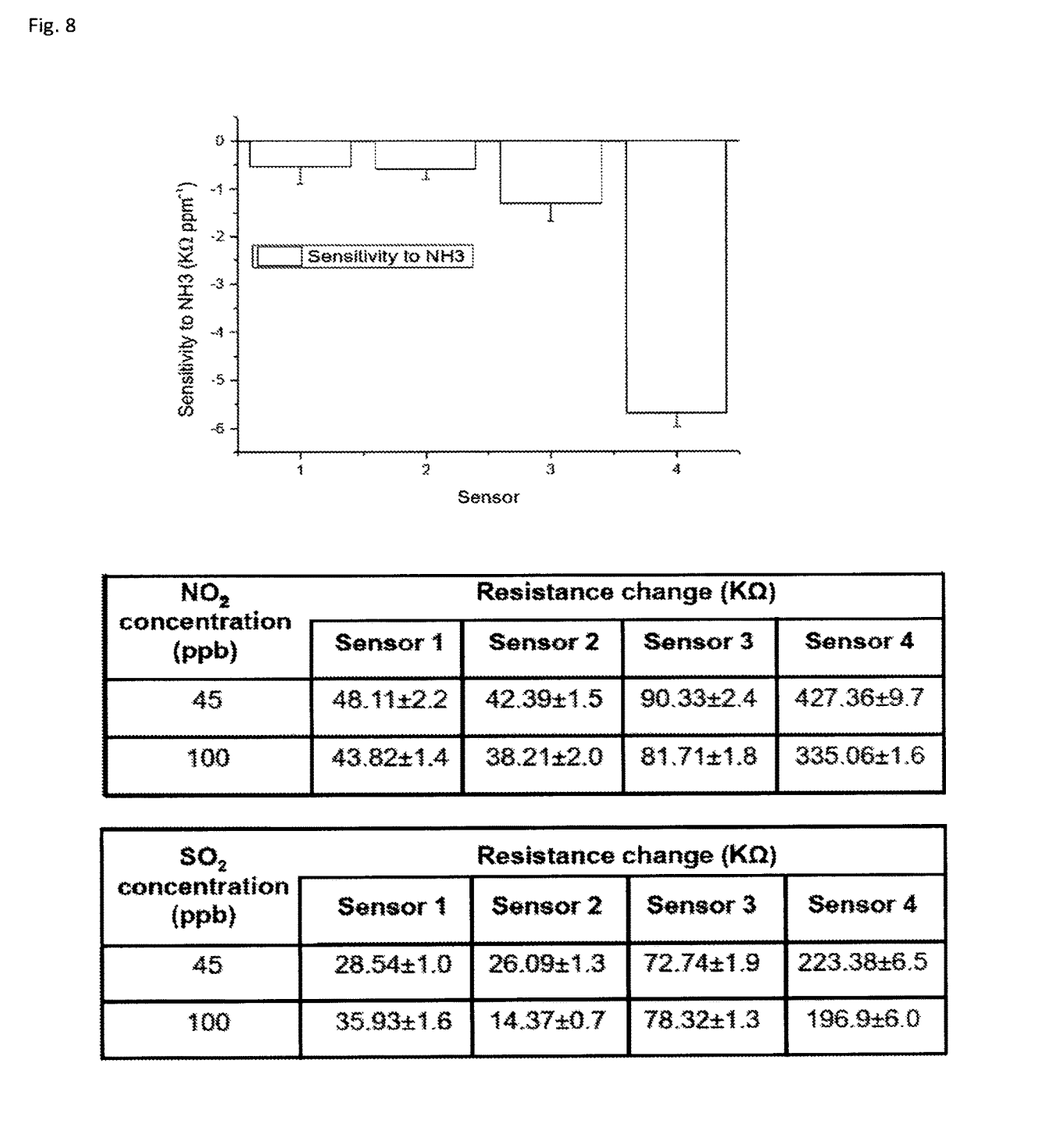

FIG. 3 shows a schematic of a sensor. The electrode structure 2 is disposed on a substrate 4. The electrodes 2 are electrically connected to a controller 6 and data processor 8 to form a functioning sensor. The sensor structure can be packaged in a relatively standard sensor packaging which includes filters and/or catalysts to break down certain species and prevent fouling of the electrode structure. Sensor functionality is via impedance measurements.

In addition to the above, it has also been found that graphene sensor electrodes such as those described herein can be driven in such a manner as to readily clean the electrode. As such, in accordance with another aspect as described herein there is provided a sensor comprising: a sensor electrode comprising graphene material; and a controller for providing a drive signal to the sensor electrode in order to sense species adhered to the sensor electrode, wherein the controller is further configured to apply a cleaning voltage to the sensor electrode, the cleaning voltage having a frequency in a range 100 Hz to 100 kHz and a magnitude in a range 1 to 60 V, optionally 1 to 20 V, to induce heating of the sensor electrode which removes one or more species adhered to the sensor electrode. The controller can be configured to vary the cleaning voltage in order to selectively remove adhered species from the sensor electrode. Alternatively, or additionally, the controller can be configured to apply a cleaning voltage to remove all adhered species. A method of cleaning or selectively removing species from a graphene sensor electrode is thus provided by varying a frequency of the drive voltage so as to heat the graphene-based sensor electrode to remove species at relatively low power.

The low power operation of graphene sensors, such as those described herein, is advantageous for certain applications. For example, low power graphene sensors can be positioned in remote or difficult to access locations and will have a longer lifetime than higher power sensor devices which will run down their power supply more quickly. Furthermore, such low power graphene sensors are more useful for hand-held and/or mobile sensor devices which utilize a finite battery power source. Further still, such low power sensor devices can be more easily run off a low power renewable power source.

In addition to the above, a sensor system can also be provided comprising at least two sensors including a graphene sensor and another sensor, wherein the system is configured such that when the graphene sensor senses a target species or a threshold level of a target species then it sends a signal to wake up the other sensor to take a sensor measurement of the same or a different target species. In this way, a low power graphene sensor can be left running for a long period of time while a higher power sensor can remain in a dormant low power state until it is woken up to take a measurement by the low power graphene sensor. For example, the higher power sensor may be more accurate and/or be capable of measuring different target species or different levels of target species. In this way, the system as a whole is low power for extended periods of time and only switches to a higher power mode when required to do so as a result of indicative measurements from the lower power graphene sensor that a measurement from the higher power sensor is required.

The sensor technology as described can be applied in a range of applications. Some examples of target species and related applications are set out below:

Ammonia—agriculture, pharmaceuticals, environmental protection, chemical industry, medical diagnostics, explosive detection, food freshness;

Nitrogen dioxide—internal combustion engines, thermal power stations, petroleum/metal refining, coal-fired power stations, other manufacturing industries, wastewater treatment plants;

Hydrogen sulphide—iron smelting, landfills, food processing plants, breweries, nuclear power plants, agriculture;

Sulphur dioxide—poultry houses, fumigation, research/labs, leak detection in process manufacturing, textiles, refrigeration/cold storage, fermentation process and packaging, coking operations, petroleum refineries, paper bleaching, chemical pulping;

Ethylene—chemical industry, agriculture (e.g. seed germination, adventitious rooting, fruit ripening, leaf shedding, leaf yellowing and flower death);

Carbon dioxide—automotive, food storage/refrigeration, flammable liquid/gas storage, classroom, general indoor air quality;

Carbon monoxide—domestic and commercial buildings, anywhere humans work/live as undetectable to the human nose.

The aforementioned applications may use a graphene sensor as described herein to sense the target species and/or use a graphene sensor to wake up a more accurate, higher power sensor for taking measurements.

The sensors as described herein are capable of detecting gas species at very low concentrations, e.g. less than 50 ppb levels of ammonia which is useful for agriculture applications.

Measurement Results

FIGS. 4 to 8 show resistance measurement results for four sensors fabricated as described herein. $NH_3$, $NO_2$ and $SO_2$ measurements were performed for each sensor.

The examples described herein are to be understood as illustrative examples of embodiments of the invention. Further embodiments and examples are envisaged. Any feature described in relation to any one example or embodiment may be used alone or in combination with other features. In addition, any feature described in relation to any one example or embodiment may also be used in combination with one or more features of any other of the examples or embodiments, or any combination of any other of the examples or embodiments. Furthermore, equivalents and modifications not described herein may also be employed within the scope of the invention, which is defined in the claims.

The invention claimed is:

1. An ink for fabricating a sensor electrode, the ink comprising:
   water;
   polyvinylpyrrolidone (PVP); and
   a graphene material;
   wherein the graphene material is in the form of a sulphur-doped graphene material, and the sulphur dopant is provided within a concentration range of 0.01 mg to 1 mg of sulphur dopant per 1 mg of graphene.

2. The ink according to claim 1, wherein the PVP has a chain length between 10 and 400, between 10 and 100 or between 10 and 60.

3. The ink according to claim 1, wherein the PVP is provided within a concentration range of 0.01 to 10 mg per ml of the ink, or within a concentration range of 0.1 to 1 mg per ml of the ink.

4. The ink according to claim 1, wherein the PVP is provided within a concentration range of 0.01 to 1 mg per mg of graphene, or within a concentration range of 0.04 to 0.4 mg per mg of graphene.

5. The ink according to claim 1, wherein the graphene material is in the form of flakes having a diameter in a range 1 to 20 micrometers, 1 to 10 micrometers or 2 to 5 micrometers.

6. The ink according to claim 1, wherein the graphene material is in the form of flakes, each flake having a variable number of atomic carbon layers thus providing binding sites at edges of atomic layers.

7. The ink according to claim 1, wherein the graphene material is in the form of a reduced graphene oxide material.

8. The ink according to claim 1, wherein the sulphur-doped graphene material is formed using a thiourea and/or sulfamic acid dopant.

9. The ink according to claim 1, wherein the sulphur dopant is provided within a concentration range of 0.15 mg-0.5 mg of sulphur dopant per 1 mg of graphene.

10. The ink according to claim 1, wherein the graphene material has a metal functionalized surface.

11. The ink according to claim 10, wherein the metal functionalized surface comprises one or more of: yttrium; iron; strontium; molybdenum; tin; cobalt; nickel; palladium; and tungsten.

12. The ink according to claim 10, wherein the metal functionalized surface comprises nanostructures.

13. The ink according to claim 10, wherein the metal functionalized surface comprises metal in the form of a metal salt, or a metal oxide.

14. The ink according to claim 1, wherein the graphene material is provided within a concentration range of 0.5 to 50 mg per ml of the water, or 1 to 10 mg per ml of the water.

15. A sensor electrode comprising:
   the ink according to claim 1 printed onto a substrate.

16. The sensor electrode according to claim 15, wherein the PVP has a chain length between 10 and 400, between 10 and 100 or between 10 and 60.

17. The sensor electrode according to claim 16, wherein the graphene material is in the form of flakes having a diameter in a range of 1 to 20 micrometers, 1 to 10 micrometers or 2 to 5 micrometers.

* * * * *